United States Patent [19]

Lien

[11] 4,150,147
[45] Apr. 17, 1979

[54] STIMULATION OF PROLACTIN RELEASE BY AN AMINOTETRALIN ANALGESIC

[75] Inventor: Eric L. Lien, Paoli, Pa.

[73] Assignee: American Home Products Corporation, New York, N.Y.

[21] Appl. No.: 889,775

[22] Filed: Mar. 24, 1978

[51] Int. Cl.² .......................................... A61K 31/135
[52] U.S. Cl. .................................................. 424/330
[58] Field of Search ........................................ 424/330

[56] References Cited

U.S. PATENT DOCUMENTS 3,836,670  9/1974  Freed et al. ........................... 424/330
4,061,737  12/1977  Alburn et al. ........................ 424/177

OTHER PUBLICATIONS

C. Rivier et al., Endocrinol., 100, p. 238 (1977).
Lien et al., Life Sci., 19 837 (1976).

Primary Examiner—Stanley J. Friedman

[57] ABSTRACT

The administration of the analgesic 13β-amino-5,6,7,8,9,10,11,12-octahydro-5α-methyl-5,11-methanobenzocyclodecen-3-ol to warm-blooded animals stimulates prolactin release.

1 Claim, No Drawings

STIMULATION OF PROLACTIN RELEASE BY AN AMINOTETRALIN ANALGESIC

This invention relates to the chemical compound (−)-13β-amino-5,6,7,8,9,10,11,12-octahydro-5α-methyl-5,11-methanobenzocyclodecen-3-ol and its use in the stimulation of prolactin release.

Prolactin is an important pituitary hormone whose physiological functions include the promotion of mammary gland development and the induction of lactation. Prolactin secretion is regulated by the thyrotropin releasing factor (throliberin or TRH) which is secreted by the hypothalamus. It is known that the administration of various substances will stimulate prolactin release; for example, the narcotic-analgesic morphine, the analgesic peptide methione-enkephalin, and certain methione-enkephalin analogs, have been demonstrated to effect release of prolactin.

The invention sought to be patented constitutes a method of stimulating prolactin release in a warm-blooded animal, in which such stimulation is desirable, which comprises administering to said animal an effective amount of the compound (−)-13β-amino-5,6,7,8,9,10,11,12-octahydro-5α-methyl-5,11-methanobenzocyclodecen-3-ol, or a non-toxic acid addition salt thereof. Preferred acid addition slats are the hydrochloride, hydrobromide, lactate, or acetate.

The compound (−)-13β-amino-5,6,7,8,9,10,11,12-octahydro-5α-methyl-5,11-methanobenzocyclodecen-3-ol, employed in the method of this invention, is an analgesic of higher potency than morphine but is non-addictive. Its preparation and method of use as an analgesic are described in U.S. Pat. No. 3,836,670.

In carrying out the method of this invention the active compound can be administered either alone or in combination with inert pharmaceutically acceptable carriers in a variety of dosage forms, orally or parenterally. The dose requirements will vary with the severity of the conditions being presented, the animal being treated, or the dosage form employed. Therapy is instituted at low dosages and the dosage is increased incrementally until the desired prolactin releasing effect is achieved.

Prolactin in blood samples can be determined by the specific double antibody radioimmunoassay method of Neill and Reichert, Endocrinology, 88, 548 (1971).

With large animals (about 70 kg. body weight) an effective dose by the parenteral route, such as by intramuscular or subcutaneous injection, is from about 05 mg. to about 50 mg., preferably about 2 mg. to about 20 mg.

For unit dosages, the active compound can be compounded into any of the usual oral or parenteral dosage forms, including tablets, capsules, elixir, or suspensions. The dosage forms can contain conventional inert pharmaceutical carriers as diluents, lubricating agents, stabilizing agents, preserving agents, or flavoring agents, as needed. Suitable pharmaceutical carrying agents and methods of preparation thereof will be apparent to those skilled in the art. In all cases, the proportion of the active ingredient in a dosage form must be sufficient to impart prolactin releasing activity thereto.

The ability of (−)-13β-amino-5,6,7,8,9,10,11,12-octahydro-5α-methyl-5,11-methanobenzocyclodecen-3-ol to stimulate prolactin release has been demonstrated in rats as described in the following example:

EXAMPLE

Male Charles River CD rats (300–350 g.) are given a subcutaneous injection of (−)-13β-amino-5,6,7,8,9,10,11,12-octahydro-5α-methyl-5,11-methanobenzocyclodecen-3-ol in saline or of saline alone (controls). Fifteen minutes later the animals are decapitated and blood is collected in Traysylol-EDTA (12 mg. EDTA in 6000 units Traysylol). Easch plasma sample is assayed for prolactin and growth hormone (GH) in triplicate by specific double antibody radioimmunoassay using NIAMDD reagents. Prolactin is determined by the method of Neill and Reichert, Endocrinology, 88, 548 (1971); GH is determined by the method of Sinha, Endocrinology, 91, 784 (1972). The results are shown in the table below:

| Treatment | Dose, μg/kg | Prolactin, ng/ml | GH, ng/ml |
|---|---|---|---|
| Saline | — | — | 27 ± 5 |
| Compound | 200 | — | 563 ± 76* |
| Saline | — | 7.5 ± 1 | 39 ± 4 |
| Compound | 1 | 11 ± 2 | 35 ± 4 |
|  | 5 | 17 ± 4 - | 59 ± 22 |
|  | 20 | 12 ± 2 - | 37 ± 4 |
|  | 100 | 14 ± 4 | 236 ± 68* |

Number of animals per group: 8
\* - $p<0.01$; - - $p<0.05$

The above results show that (−)-13β-amino-5,6,7,8,9,10,11,12-octohydro-5α-methyl-5,11-methanobenzocyclodecen-3-ol in rats by subcutaneous administration produces a statistically significant rise in serum prolactin levels at a dose of 5 and 20 mg/kg. At a dose of 100 and 200 μg/kg. the compound produces statistically significant increase in serum growth hormone levels.

What is claimed is:

1. A method of stimulating prolactin release in a warm-blooded animal, in which such stimulation is desirable, which comprises administering to said animal an effective amount of the compound (−)-13β-amino-5,6,7,8,9,10,11,12-octahydro-5α-methyl-5,11-methanobenzocyclodecen-3-ol, or a non-toxic acid addition salt thereof.

* * * * *